(12) United States Patent
Larsen et al.

(10) Patent No.: US 8,529,518 B2
(45) Date of Patent: Sep. 10, 2013

(54) DRUG DELIVERY DEVICE WITH CAP FUNCTIONS FOR NEEDLE ASSEMBLY

(75) Inventors: Andre Larsen, Dragor (DK); Karsten Baker Nielsen, Copenhagen O (DK); Thibaud Hofstatter, Helsingor (DK); Omid Reza Hissinian, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 3 days.

(21) Appl. No.: 13/376,696

(22) PCT Filed: Jun. 14, 2010

(86) PCT No.: PCT/EP2010/058322
§ 371 (c)(1),
(2), (4) Date: Mar. 16, 2012

(87) PCT Pub. No.: WO2010/142813
PCT Pub. Date: Dec. 16, 2010

(65) Prior Publication Data
US 2012/0191046 A1 Jul. 26, 2012

Related U.S. Application Data

(60) Provisional application No. 61/186,550, filed on Jun. 12, 2009, provisional application No. 61/258,040, filed on Nov. 4, 2009.

(30) Foreign Application Priority Data

Jun. 12, 2009 (EP) .................................... 09162593
Sep. 21, 2009 (EP) .................................... 09170836
Oct. 29, 2009 (EP) .................................... 09174414

(51) Int. Cl.
*A61M 5/32* (2006.01)

(52) U.S. Cl.
USPC .......................................... 604/192; 604/263

(58) Field of Classification Search
USPC ......................... 604/192–193, 197–198, 263
See application file for complete search history.

(56) References Cited

U.S. PATENT DOCUMENTS

| 5,693,027 A | 12/1997 | Hansen et al. |
| 5,873,856 A * | 2/1999 | Hjertman et al. ............. 604/117 |
| 6,126,646 A | 10/2000 | Hansen et al. |

(Continued)

FOREIGN PATENT DOCUMENTS

| EP | 903157 A2 | 3/1999 |
| EP | 1690562 A1 | 8/2006 |

(Continued)

*Primary Examiner* — Quynh-Nhu H Vu
(74) *Attorney, Agent, or Firm* — Marc A. Began

(57) ABSTRACT

Drug delivery system comprising a main portion with a cap as well as a needle assembly with a needle mounted in a hub and a needle cap releasably mountable on the hub to cover the needle. The cap comprises gripping means reversibly operatable between a first condition in which there is no gripping engagement between the mounted cap portion and the needle cap, this allowing the cap portion to be removed from the main portion without removing the needle cap from the hub, and a second condition in which the cap portion grippingly can engage the needle cap of a needle assembly, this allowing the needle cap to be removed from the hub together with the cap. The cap further comprises user actuation means for operating the gripping means between the two conditions.

14 Claims, 15 Drawing Sheets

(56) References Cited

U.S. PATENT DOCUMENTS

| | | |
|---|---|---|
| 7,094,223 B2 | 8/2006 | Brunel |
| 7,449,012 B2 | 11/2008 | Young et al. |
| 7,815,611 B2 * | 10/2010 | Giambattista et al. ........ 604/198 |
| 2008/0015519 A1 | 1/2008 | Klint et al. |
| 2008/0103453 A1 * | 5/2008 | Liversidge .................... 604/187 |
| 2009/0069753 A1 * | 3/2009 | Ruan et al. .................... 604/192 |

FOREIGN PATENT DOCUMENTS

| | | |
|---|---|---|
| EP | 2033672 A2 | 3/2009 |
| WO | 97/48430 A1 | 12/1997 |
| WO | 2005/115508 A1 | 12/2005 |
| WO | 2006/032385 A1 | 3/2006 |
| WO | 2007/036676 A1 | 4/2007 |
| WO | 2007/138296 A1 | 12/2007 |
| WO | 2007/138299 A1 | 12/2007 |

* cited by examiner

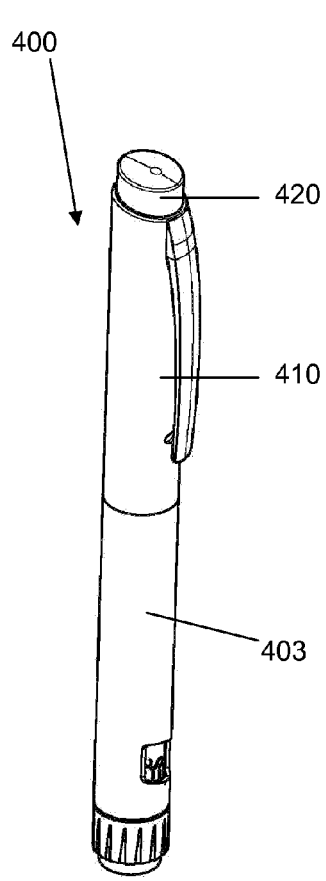 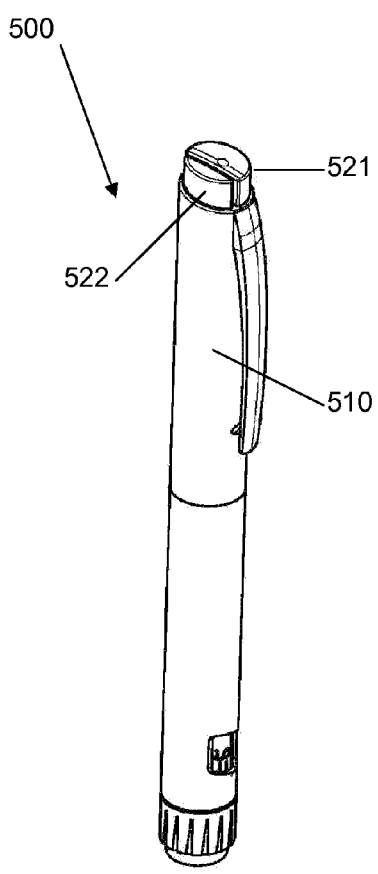 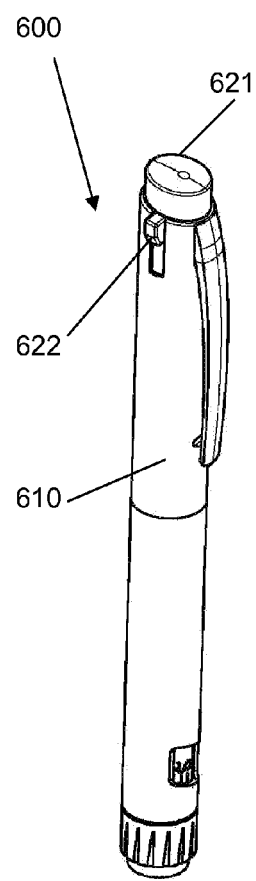
Fig. 16                    Fig. 17                    Fig. 18

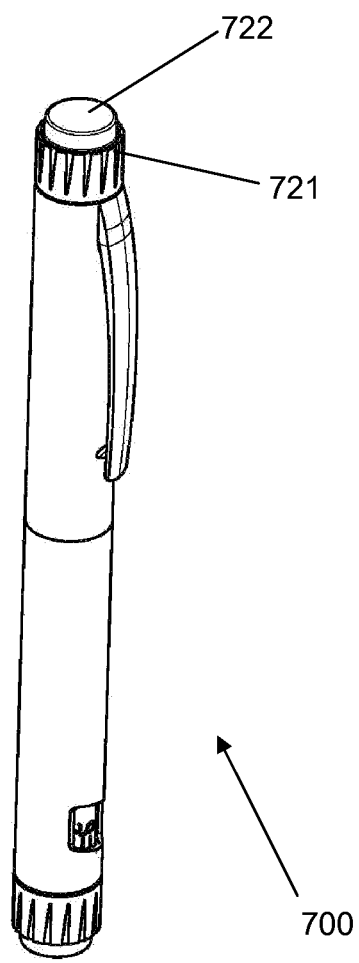
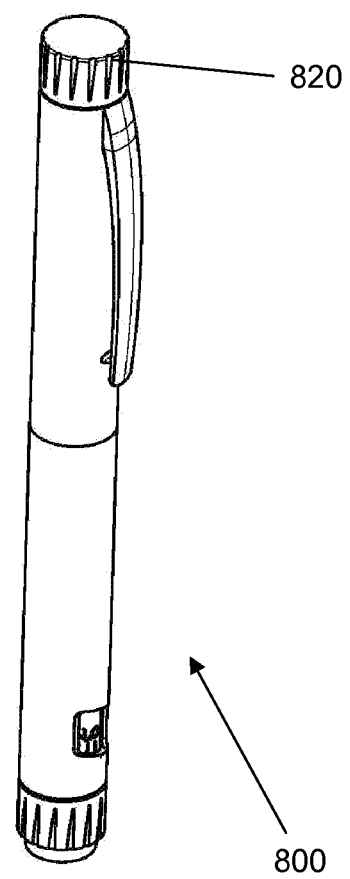
Fig. 19
Fig. 20

DRUG DELIVERY DEVICE WITH CAP FUNCTIONS FOR NEEDLE ASSEMBLY

CROSS-REFERENCE TO RELATED APPLICATIONS

This application is a 35 U.S.C. §371 national stage application of International Patent Application PCT/EP2010/058322 (published as WO 2010/142813), filed Jun. 14, 2010, which claimed priority of European Patent Application 09162593.9, filed Jun. 12, 2009, European Patent Application 09170836.2, filed Sep. 21, 2009, and European Patent Application 09174414.4, filed Oct. 29, 2009; this application further claims priority under 35 U.S.C. §119 of U.S. Provisional Application 61/186,550, filed Jun. 12, 2009 and U.S. Provisional Application 61/258,040, filed Nov. 4, 2009.

The present invention generally relates to medical delivery devices. In specific embodiments the invention relates to medical delivery devices adapted for mounting of a transcutaneous needle device.

BACKGROUND OF THE INVENTION

In the disclosure of the present invention reference is mostly made to the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be highly sophisticated electronically controlled instruments with numerous functions. Regardless of their form, they have proven to be great aids in assisting patients to self-administer injectable drugs and biological agents. They also greatly assist care givers in administering injectable medicines to those incapable of performing self-injections.

In particular pen-style injection devices have proven to provide an accurate, convenient, and often discrete, way to administer drugs and biological agents, such as insulin. Modern devices have become more sophisticated and often include diverse and robust functions, such as memories for remembering time and amount of last dose, as well as, in the case of insulin devices, blood glucose monitors. While pen-style injection devices are typically cylindrically shaped with a needle protruding from the most distal portion of one end of the device, some devices have other shapes with the needle no longer protruding from the most distal part of an end of the device, e.g. Innovo® and InnoLet® from Novo Nordisk A/S Bagsvaerd Denmark.

Typically, injection devices use a pre-filled cartridge containing the medication of interest, e.g. 1.5 or 3.0 ml of insulin or growth hormone. The cartridge is typically in the form of a generally cylindrical transparent ampoule with a needle pierceable septum at one end and an opposed piston designed to be moved by the dosing mechanism of the injection device. The injection devices generally are of two types: "Durable" devices and "disposable" devices. A durable device is designed to allow a user to replace one cartridge with another cartridge, typically a new cartridge in place of an empty cartridge. In contrast, a disposable device is provided with an integrated cartridge which cannot be replaced by the user; when the cartridge is empty the entire device is discarded. Most injection devices are provided with a releasable pen cap covering the cartridge and the needle mount portion (see below), this allowing the user to inspect the content of the cartridge by removing the cap.

Cartridge-based drug delivery devices are typically designed for use with replaceable subcutaneous needle assemblies allowing a user to mount a fresh and sterile needle before each subcutaneous injection, however, many users decide to use a needle assembly more than one time. To allow a needle assembly to be mounted in fluid communication with the cartridge through the needle-pierceable septum, the injection device is provided with a needle mount which may be formed either as part of the device or as part of the cartridge, see e.g. U.S. Pat. Nos. 5,693,027 and 6,126,646, which are hereby incorporated by reference.

A typical subcutaneous injection needle assembly designed for use with a drug delivery device comprises a fine needle mounted in a hub having coupling means allowing the hub to be mounted on the injection device, thereby introducing the distal end of the needle through the cartridge septum. The hub may be cup-shaped with the inner mounting means adapted to engage corresponding mounting means on the injection device, e.g. a threaded connection or a bayonet coupling as disclosed in US 2008/0015519. The needle is normally provided in a container having an opening sealed by a peelable membrane, the container being in releasable, e.g. frictional, engagement with the needle hub. The coupling between container and hub allows the container to be used as a mounting tool when the membrane has been peeled off, just as it can be used as a tool for removing the needle after use. To further protect the pointed distal end of the needle and prevent unintentional user contact with the needle a needle cap is mounted on the hub covering the distal end of the needle. The needle cap will normally be removed just prior to use and remounted just after. Indeed, in case a user decides to remove the needle assembly from the injection device after an injection the container can be mounted on the needle assembly without the needle cap being in place. As many users prefer to use a needle assembly more than once the cap is normally designed to house a needle assembly including the needle cap. Indeed, this feature also allows a user to mount a fresh needle assembly in advance.

As appears from the above, the mounting and use of disposable needle assemblies in connection with the use of drug delivery devices involves handling and keeping track of a number of members, e.g. the needle cap needs handling almost every time an injection is taking place. Further, to inspect the content of the cartridge or confirm that a needle is mounted a user has to remove the pen cap.

Having regard to the above, it is an object of the present invention to provide devices and methods allowing secure and easy operation of a drug delivery system comprising a drug delivery device with a reservoir and a thereto mountable needle assembly.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, a drug delivery system comprising or being adapted to cooperate with a needle assembly is provided, the needle assembly comprising a needle hub adapted to be mounted on the main portion, a hollow needle mounted in the needle hub and comprising a distal pointed end and a proximal end, the proximal end being adapted to be arranged in fluid communication with the reservoir when the hub is mounted on the main portion, and a needle cap releasably mountable on the hub to cover the distal pointed end. The drug delivery system comprising a main portion comprising a drug reservoir or means for receiving a drug reservoir, and drug expelling means for expelling drug from the reservoir, the drug delivery system further comprising a cap portion (which may be named a pen cap when the drug delivery system has a general pen form) releasably mountable to the main portion and comprising first gripping means reversibly operatable between (i) a first state in which there is no gripping engagement between the first gripping means of a mounted cap portion and a given first part of a needle assembly when the needle assembly is mounted on the main portion, this allowing the cap portion to be removed from the main portion without removing the given first part from the main portion, and (ii) a second state in which the first gripping means of the cap portion grippingly can engage the given first part of a needle assembly mounted on the main portion, this allowing the cap portion to be removed from the main portion together with the given first part when the cap portion is removed from the main portion, the cap portion further comprising first user actuation means for operating the first gripping means between the two states.

By the above arrangement it is possible to (i) reduce the number items handled during normal use of a drug delivery system comprising a needle assembly, (ii) reduce the number of handling steps during normal operation of the needle assembly, (iii) reducing the risk of contaminating the needle, (iv) reducing the risk of loosing the needle cap and/or needle hub, and (v) reduce the risk of injuries. More specifically, when the given first part is a needle cap, by allowing the user to remove and mount the needle cap on the needle hub together with the cap portion fewer handling steps are necessary. As the needle cap is mounted inside the cap it is better protected against contamination as well as getting lost. Further, by using the cap portion as a handling tool for the relatively small needle cap during remounting on the needle hub, the risk of accidental needle injuries is reduced. Further, the interface between the cap portion and the main portion may be designed in such a way that the risk of damaging the needle with the needle cap is reduced or removed.

When the given first part is a needle cap, the cap portion may further comprise second gripping means reversibly operatable between (i) a first state in which there is no gripping engagement between the second gripping means of a mounted cap portion and a needle hub of a needle assembly when the needle assembly is mounted on the main portion, this allowing the cap portion to be removed from the main portion without removing the needle hub from the main portion, and (ii) a second state in which the second gripping means of the cap portion grippingly can engage the needle hub of a needle assembly mounted on the main portion, this allowing the needle hub to be demounted from the main portion and the cap portion to be removed from the main portion together with the demounted needle hub, as well as second user actuation means for operating the second gripping means between the two states.

In a specific embodiment, the first and second user actuation means are combined in a common user actuation means serving to actuate both the first and second gripping means. In this case the second gripping means in their actuated state may be adapted to disengage a still mounted needle hub when the cap portion is removed from the main portion.

The above-described cap portions may comprise additional gripping means adapted to provide a gripping engagement between the cap portion and a mounted needle cap, the additional gripping means providing a grip which is sufficiently strong to hold a needle cap in gripping engagement with the cap portion after a needle cap has been removed from a needle hub mounted on the main portion, and sufficiently weak to allow the cap portion to be removed from the main portion without removing a needle cap from a needle hub mounted on the main portion. In this way it is secured that a needle cap will not accidentally fall out of the cap portion.

Alternatively, the above-described cap portions may comprise additional gripping means reversibly operatable between (i) a first state in which the additional gripping means provides a gripping engagement between the cap portion and a mounted needle cap which is sufficiently strong to hold the needle cap in gripping engagement with the cap portion after the needle cap has been removed from a needle hub mounted on the main portion, or the needle hub on which the needle cap is mounted has been removed from the main portion, and sufficiently weak to allow the cap portion to be removed from the main portion without removing the needle cap from a needle hub mounted on the main portion, and (ii) a second state in which there is no gripping engagement between the additional gripping means and the needle cap, this allowing the needle cap to be removed from the cap portion after the cap portion has been removed from the main portion, as well as additional user actuation means for operating the additional gripping means between the two states.

The cap portion may have an initial state in which at least one gripping means is in the first non-gripping state, and an actuated state in which the at least one gripping means is in the second gripping state. For example, the first and/or the second gripping means may initially be in a non-gripping state, whereas the additional gripping means may initially be in a non-gripping state.

The cap portion may comprises an outer housing or shell portion with at least one pair of actuation areas (e.g. opposed to each other) serving as actuation means for associated gripping means, such that movement of a pair of actuation areas towards each other operates the associated gripping means between the initial and the actuated state.

The outer housing portion may be flexible and at least one gripping means and the thereto associated actuation means is formed integrally therewith, whereby actuation of the at least one gripping means is based on flexible deformation of the outer housing portion by means of the associated pair of actuation areas. Thus the cap portion provided with one, two or three gripping systems can be manufactured as e.g. a single injection-moulded member. Alternatively the cap may be provided with separate button members acting to move gripping structures into engagement with the needle cap, such an arrangement providing full control over the two gripping systems.

When the given first part is a needle hub the first gripping means may be reversibly operatable between (i) a first state in which there is no gripping engagement between the mounted cap portion and a needle hub when a needle assembly is mounted on the main portion, (ii) a second state in which the mounted cap portion grippingly engages a needle hub of a needle assembly mounted on the main portion, this allowing the needle assembly to be de-mounted and removed from the main portion together with the cap portion when the cap portion is removed from the main portion, and (iii) a third state in which a needle hub held in gripping engagement by the gripping means is released from the gripping means, this allowing the needle assembly to be removed from the cap portion, wherein the first user actuation means is adapted for operating the first gripping means between the three states. In such an arrangement the first gripping means may be adapted to be locked in the second state. The cap portion may comprise a cap body having release means, the first gripping means being operated between the second and third states by movement of the gripping means relative to the cap body release means.

To further improve handling and convenience the cap portion may be provided with one or more inspection openings or windows allowing a user to inspect at least a portion of a mounted needle assembly. In this way a user does not have to remove the cap to check if a needle assembly is mounted or to check the reservoir.

Correspondingly, the main portion may be provided with a user-inspectable portion adapted to be covered by the cap portion in a mounted position, the cap portion being provided with one or more inspection openings or windows allowing a user to inspect at least a portion of the user-inspectable portion when the cap portion is mounted on the main portion.

For example, the user-inspectable portion may comprise a transparent reservoir portion allowing a user to inspect drug contained in the reservoir or the position of a piston located in the reservoir. For easier inspection of the transparent reservoir the cap may be provided with a second set of inspection openings or windows arranged generally opposite the first set, this allowing light to travel through the reservoir. In a system in which at least two main portions containing different types of drugs are provided, the user-inspectable reservoir portion may comprise a colour coding indicating the type of drug contained in the reservoir.

The cap may be generally non-transparent and be provided with one or more transparent windows, the transparent windows comprising means for reducing transmission of light detrimental to drug contained in the reservoir, e.g. a UV filter. The cap may optionally be provided with the additional features described in respect of the second aspect of the invention.

In the above disclosure of aspects of the invention a system has been described, this indicating that the invention may be in the form of separate components, e.g. a drug delivery device and one or more needle assemblies adapted to be mounted on the drug delivery device, the latter comprising a main and a cap portion. In an assembled state the invention would provide a drug delivery device comprising (a) a main portion comprising a reservoir for a drug, and a drug expelling mechanism for expelling drug from the reservoir, (b) a needle assembly comprising a hub mounted on the main portion, a hollow needle mounted in the hub and comprising a distal pointed end and a proximal end arranged in fluid communication with the reservoir, and a needle cap releasably mounted to the hub and covering the distal pointed end. The device further comprises (c) a cap portion releasably mounted to the main portion and comprising gripping means as described above.

In the above described embodiments the main portion of the drug delivery device comprises a reservoir, however, in alternative versions the different embodiments may be adapted to receive a replaceable reservoir, e.g. a cartridge to be used in combination with a durable type injection device.

As used herein, the term "drug" is meant to encompass any drug-containing flowable medicine capable of being passed through a delivery means such as a cannula or hollow needle in a controlled manner, such as a liquid, solution, gel or fine suspension. Representative drugs include pharmaceuticals such as peptides (e.g. insulins, insulin containing drugs, GLP-1 containing drugs as well as derivates thereof), proteins, and hormones, biologically derived or active agents, hormonal and gene based agents, nutritional formulas and other substances in both solid (dispensed) or liquid form. In the description of the exemplary embodiments reference will be made to the use of insulin containing drugs. Correspondingly, the term "subcutaneous" infusion is meant to encompass any method of transcutaneous delivery to a subject.

BRIEF DESCRIPTION OF THE DRAWINGS

In the following the invention will be further described with reference to the drawings, wherein FIGS. 16-20 show alternative embodiments of a drug delivery device comprising pen caps adapted to engage a needle assembly.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

Figure 1:
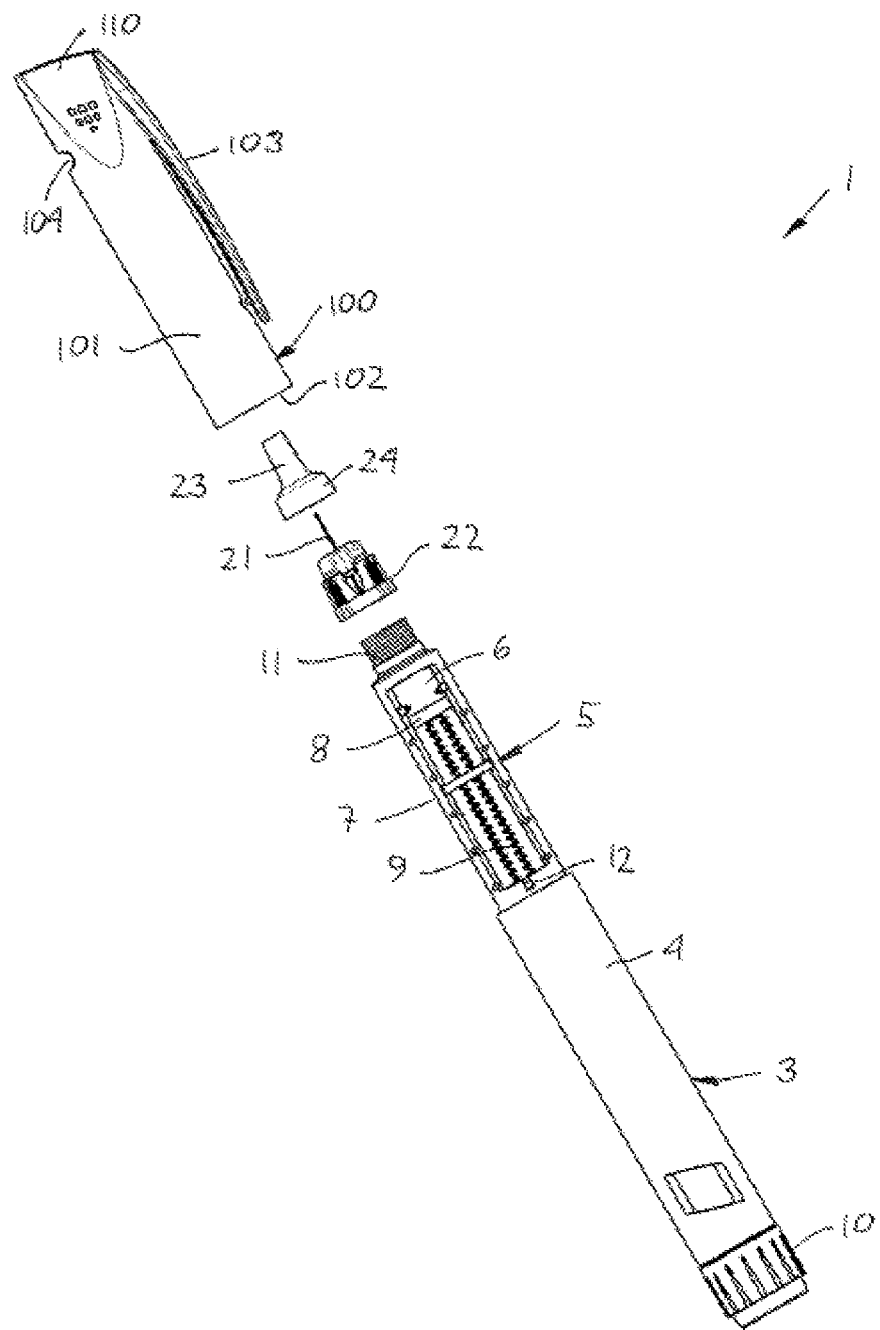
FIG. 1 shows a first embodiment of a drug delivery pen and a needle assembly.

Referring to FIG. 1 a pen-formed drug delivery device 1 will be described. The pen comprises a cap portion (or "pen cap") 100 and a main portion 3 having a proximal part 4 in which a drug expelling mechanism is arranged, and a distal reservoir part 5 in which a drug-filled transparent cartridge 6 with a distal needle-penetratable septum is arranged and hold in place by a cartridge holder 7 mounted to the proximal part, the cartridge holder having openings allowing a portion of the cartridge to be inspected. The cartridge is provided with a piston 8 driven by a piston rod 9 forming part of the expelling mechanism. A proximal-most button 10 serves to manually set and expel a desired dose of drug. This type of a pen-formed drug delivery device is well known, see e.g. WO 99/38554 to which reference is made for further details in respect of the internal construction of the shown type of pen. In the shown embodiment the pen is a disposable pre-filled device in which the cartridge holder is permanently attached to the proximal part of the main part, the cartridge holder being provided with distal coupling means in the form of a hub mount 11 having, in the shown example, an external thread adapted to engage an inner thread of a needle assembly, see below. Alternatively the pen may be a "durable" device in which the cartridge holder is releasably attached to the main part, this allowing the piston rod to be pushed back and a new cartridge to be mounted. In such an arrangement the connection for the needle assembly may be part of the cartridge. The pen cap 100 made from a non-transparent material comprises a generally cylindrical sleeve or housing 101 with a proximal closed end and a distal opening 102, a pocket clip 103 and an inspection opening 104. The proximal end is provided with two opposed generally planar gripping surfaces 110.

FIG. 1 further shows a needle assembly comprising a hollow infusion needle 21 mounted a cup-formed hub 22 with an inner coupling means in the form of a thread adapted to connect to the external thread of the pen device hub mount 11. The needle comprises a distal pointed portion protruding from the hub as well as a proximal pointed portion adapted to penetrate the cartridge septum when the hub 22 is mounted on the thread. In an alternative embodiment a bayonet coupling may be used instead of the threaded connection, e.g. the cup may be provided with a plurality of inwardly projecting protrusions (see FIG. 6) adapted to engage corresponding grooves formed distally on the pen device. The needle assembly further comprises a needle cap 23 with a skirt portion 24 adapted to releasably engage the hub to thereby protect the distal end of the needle. The needle is normally provided sterile in a container (not shown) having an opening sealed by a peelable membrane, the container being in releasable, e.g. frictional, engagement with the needle hub. The pen-formed drug delivery device 1 and the needle assembly together form a system.

Figure 2:
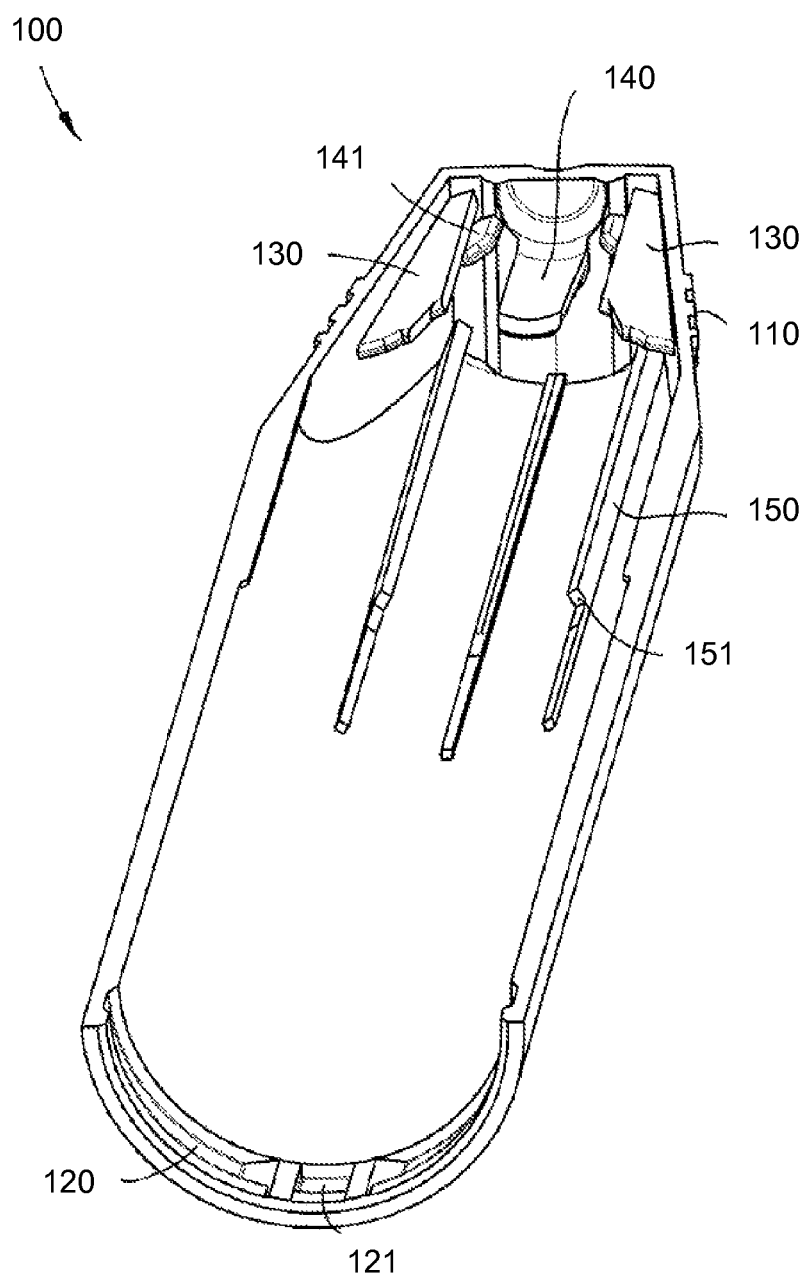
FIG. 2 shows in a cross-sectional view a pen cap.
Figure 3:
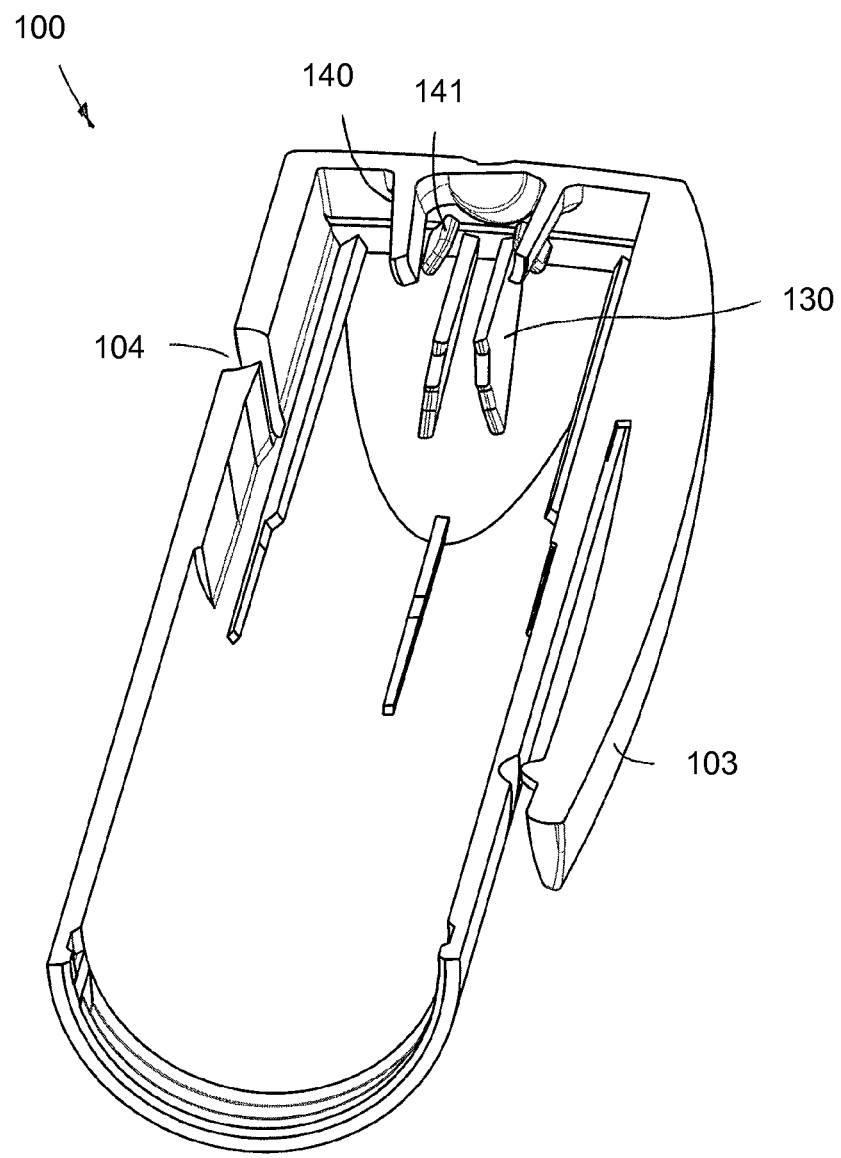
FIG. 3 shows in a cross-sectional view a pen cap as in FIG. 2, the cross-section being rotated axially 90 degrees.

Turning to FIGS. 2 and 3 showing sectional views of the pen cap 100, the pen cap is provided with coupling means 120, 121 at the distal end for releasably engaging corresponding coupling structures 12 on the main portion, as well as a number of structures adapted to engage a needle cap. More specifically, the pen cap is provided with two pairs of gripping ribs 130 arranged corresponding to the inner side of the gripping surfaces 110. As the pen cap is manufactured from a relatively flexible polymeric material forcing the two gripping surfaces against each other, e.g. when gripping the pen cap with the first and second fingers, the two pairs of ribs will be moved against each other and thus into engagement with a needle cap when the latter is placed there between, this allowing the needle cap to be removed from the needle hub, see below. Alternatively the cap may be provided with a button member acting to move a gripping structure into engagement with the needle cap. The pen cap further comprises a pair of gripping flanges 140 adapted to engage and hold the needle cap in place inside the pen cap when it has been removed from the needle hub, however, these gripping flanges do not ensure a grip strong enough to remove the needle cap from the needle hub. Protrusions 141 projecting from the closed end of the cap assure correct sideways positioning of a needle cap. In the shown embodiment the pen cap is further provided with a plurality of longitudinal ribs 150 serving to sideways position a mounted hub, each rib having a step configuration with a distally facing surface 151, this allowing the pen cap to be coded to fit only on a correspondingly designed cartridge holder 7. This may be useful in case the pen cap is e.g. colour coded corresponding to the type of drug contained in the pen device for which the cap is intended to be used with.

Figure 4:
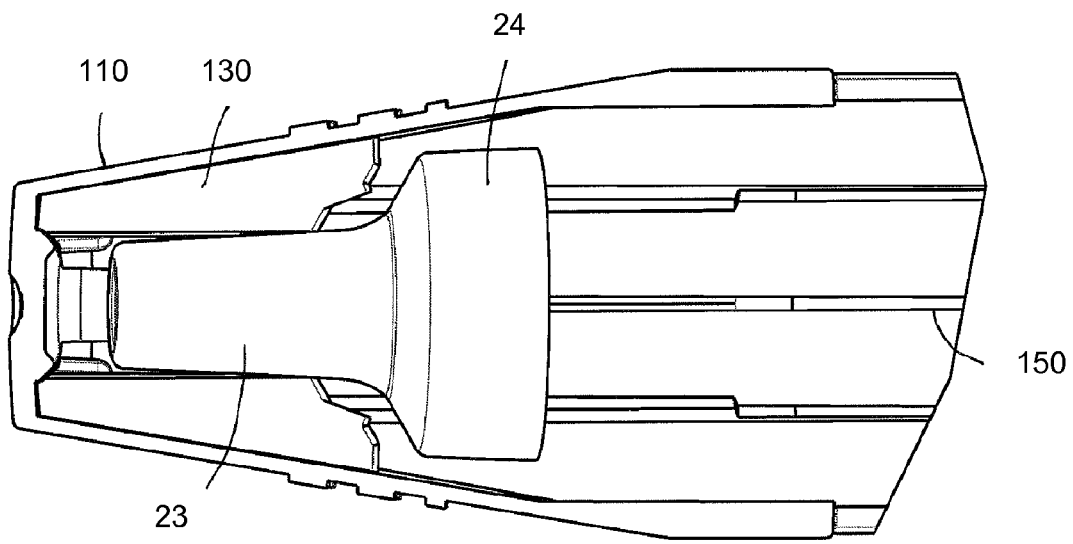
FIG. 4 shows a partial cross-sectional view of the pen cap of FIG. 2 wherein a needle cap is arranged in the interior of the cap.

FIG. 4 shows a needle cap 23 arranged inside the pen cap 100 corresponding to a position in which a needle assembly and the pen cap are mounted on the pen main portion. The two gripping surfaces 110 as well as the gripping ribs 130 are in their initial relaxed position in which there is no engagement between the pen cap and the needle cap.

Figure 5:
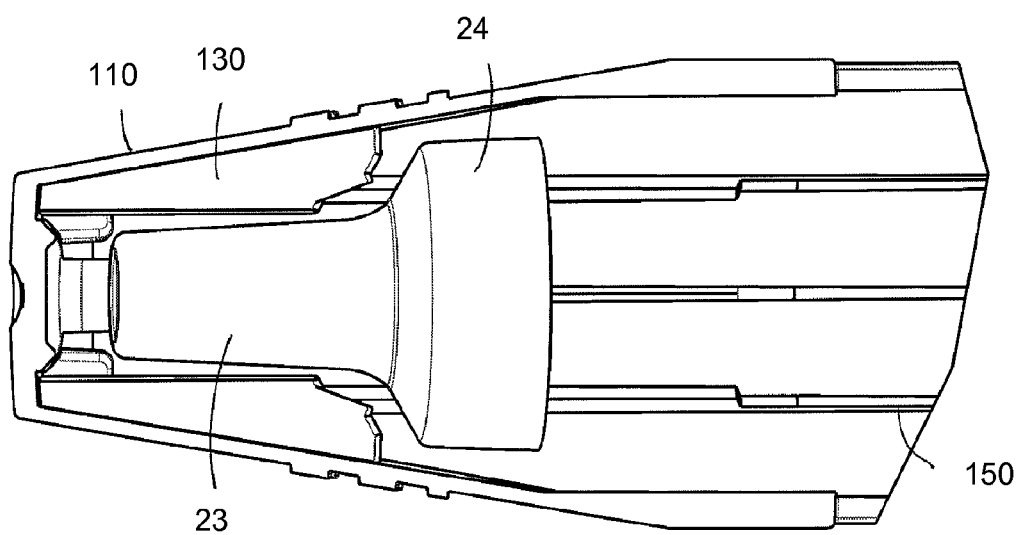
FIG. 5 shows the pen cap and needle cap of FIG. 4 in gripping engagement.

In FIG. 5 the two gripping surfaces 110 have been moved against each other, thereby providing a gripping engagement between the pen cap and the needle cap, this allowing in a situation of use the needle cap to be removed from the needle hub when the pen cap is removed from the pen main portion. When the user relaxes the pressure on the gripping surfaces 110 the gripping flanges 140 serve to hold the needle cap properly in place until it is time put on the pen cap again. The inspection opening 104 is arranged in such a way that a user can control if the skirt portion 24 of the needle cap is in place without having to take off the pen cap. If a needle assembly is mounted but the needle cap is missing the user will be able to see the distal portion of the needle hub through the opening whereas the needle cap will appear "empty" if no needle hub is mounted, i.e. when the pen cap is mounted on the pen main portion the opening 104 is positioned distally of the distal end of the coupling means 11.

As appears, the gripping flanges 140 are designed to engage and hold the needle cap until it is mounted on a needle hub again. If a user would remove a needle cap without first mounting it on a needle hub the user would hold the pen cap with the open end downwards and tap it against a solid surface until the needle cap would disengage and drop out. Alternatively, the pen cap could be provided with user actuatable additional gripping means, e.g. of the type described below in context with the FIG. 6 embodiment, this providing improved user control and ease of use.

As shown in FIG. 2 the cap may be provided with coupling means 120, 121 for mounting the cap on the main portion. In the shown embodiment a circumferential groove 120 assures that the cap can be axially locked in place, whereas a second type of coupling in the form of one or more indentations 121 assures that the cap can be locked rotationally. Providing e.g. 4 indentations at 90 degrees spacing the cap portion could be rotated between a first and a second mounted position, the first position placing the openings 260 over the cartridge holder 7 thereby blocking for light, with the second position placing the openings over the transparent cartridge this allowing a user to inspect the reservoir.

With reference to FIGS. 6-10 a further pen cap 900 will be described, the pen cap as in the FIG. 2 embodiment being provided with coupling means at the open end (not shown) for releasably engaging corresponding coupling structures 12 on a drug delivery device main portion, as well as a number of additional structures adapted to engage components of a needle assembly comprising a needle hub and a needle cap.

More specifically, the pen cap 900 comprises a cap housing 901 provided with three systems of gripping means: First gripping means for gripping a needle cap, second gripping means for gripping a needle hub, and additional gripping means for holding a needle cap in place when the pen cap has been removed from a main portion, the gripping function being controlled by user actuation means.

Figure 6:
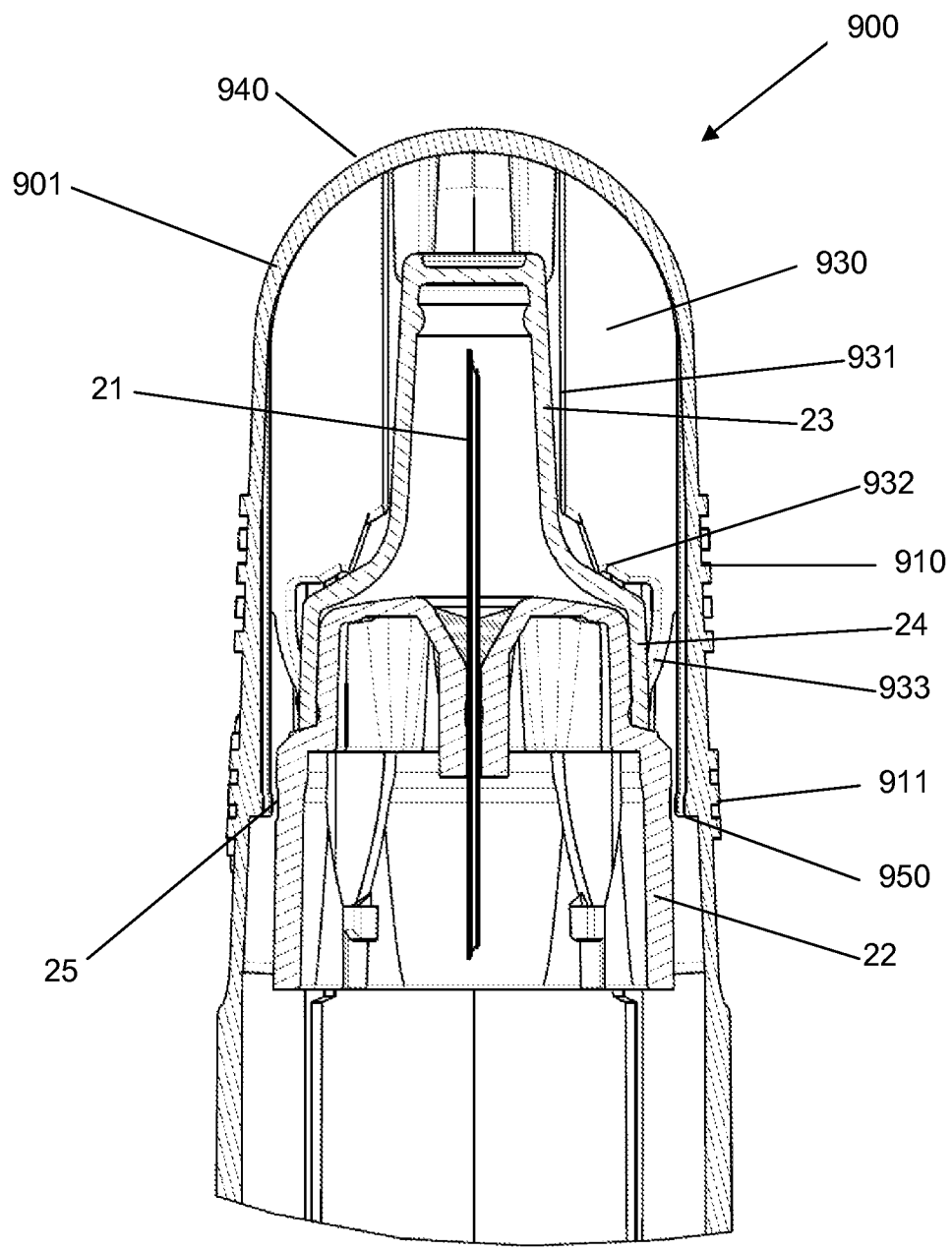
FIG. 6 shows a partial longitudinal cross-sectional view of a further pen cap in which a needle assembly is mounted.
Figure 10:
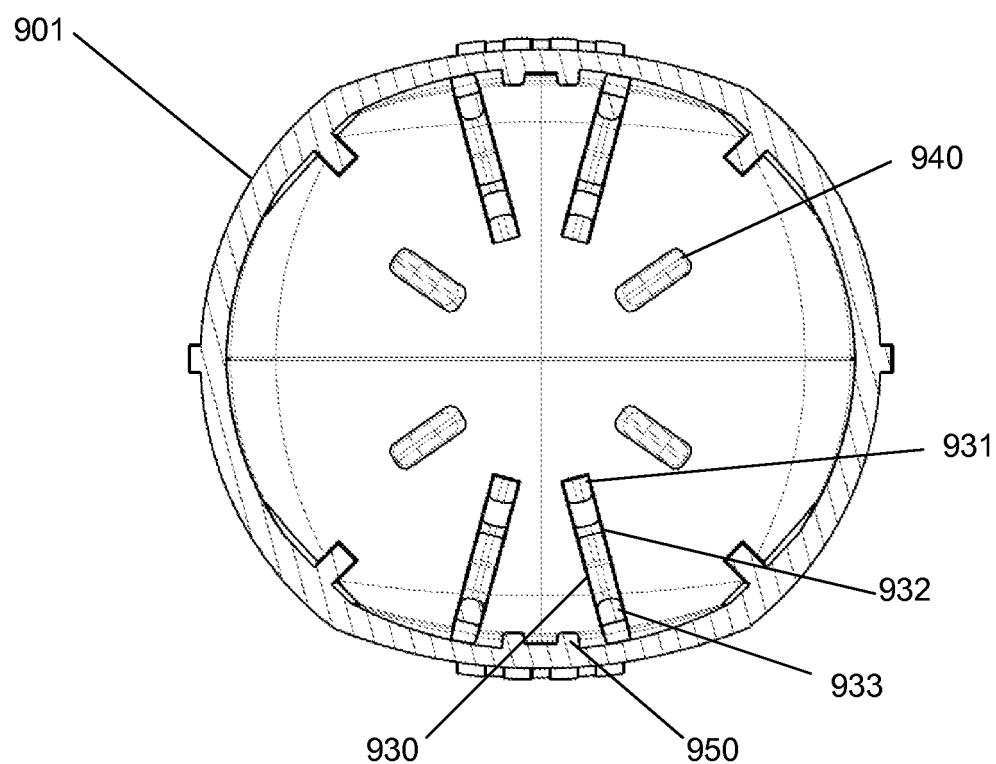
FIG. 10 shows a transversal cross-sectional view of the pen cap of FIG. 6.

Turning to FIGS. 6 and 10 two pairs of gripping ribs 930 are arranged corresponding to the inner side of a pair of first opposed actuation surfaces 910. Each rib comprises a gripping edge 931 adapted to engage the distal tubular portion 23 of a needle cap, a proximally facing projection 932 adapted to engage the distally facing surface of skirt portion 24 of the needle cap, and a flexible arm 933 adapted to engage the outwards facing surface of skirt portion 24 of the needle cap (see below). When actuated, the grip between the pen cap gripping edges 931 and the needle cap shall ensure that the needle cap can be released from its gripping engagement with a needle hub coupled to the main portion. In the shown embodiment the grip is frictional, however, in alternative embodiments the grip may be provided with corresponding coupling structures on the pen cap and needle cap respectively. Inner protrusions 940 projecting from the closed end of the cap assure correct sideways positioning of a needle cap.

The cap is further provided with two pairs of relatively short gripping projections 950 arranged corresponding to the inner side of a pair of second opposed actuation surfaces 911, the projections being adapted to engage the outwards facing surface of the cup-formed hub 22 of a needle assembly. In the shown embodiment the hub is provided with a circumferential relatively shallow groove (or circumferential groove portions) into which the projections are moved when actuated. When actuated, the grip between the pen cap projections 950 and the needle hub shall ensure that the needle hub can be rotated together with the pen cap in order to release the needle hub from the main portion. Depending on whether a bayonet coupling or a threaded connection is provided the cap may have to be rotated just a little, e.g. 45 degrees, or several times. Further, when the needle hub has been released from the hub mount 11 the grip between the pen cap projections 950 and the needle hub shall ensure that the needle hub can be moved axially away from the main portion together with the pen cap. In case a bayonet coupling is provided the needle hub will normally not move axially when twisted to disengage the hub mount 11, this allowing for a simpler construction of the pen cap as the pen cap will not have to accommodate the axial movement of a needle assembly being unscrewed. Alternatively, the user would have to unscrew the pen cap from the main portion together with the needle hub.

In the shown embodiment the pen cap housing 901 is manufactured from a relatively flexible polymeric material. Thus, forcing two opposed actuation surfaces 910, 911 against each other, e.g. when gripping the pen cap with the first and second fingers, the pen cap will be squeezed oval and the underlying gripping means (i.e. gripping edges 931 or gripping projections 950) will be moved against in each other and thus into engagement with a needle cap respectively the needle hub when the latter are placed there between, this allowing the needle cap respectively the needle hub to be removed from the needle hub respectively the main portion, see below. However, depending on the actual design of the pen cap it may be found that actuation of one pair of actuation surfaces will actually actuate both gripping systems. Correspondingly, in the shown embodiment the axial grip between the second gripping means and the needle hub is relatively weak allowing the actuated second gripping means to be axially pulled out of engagement in case the needle hub is still coupled to the main portion. Thus, the two pairs of opposed actuation surfaces may be replaced by a single pair of actuation surfaces (e.g. placed axially between the two pairs shown in FIG. 6), this providing a simplified user interface. Alternatively the cap may be provided with separate first and second button members acting to move gripping structures into engagement with the needle cap, such an arrangement providing full control over the two gripping systems.

The above-described flexible arms 933 provide the additional gripping means (or holding means) and are associated with a third pair of opposed actuation surfaces (not shown) offset 90 degrees relative to the other gripping means. Thus, when forcing the third pair of opposed actuation surfaces against each other the flexible pen cap will be squeezed oval by which action the arms 933 will be moved away from each other and thereby disengage a mounted needle cab. It is to be noted that the drawing software used to create the present drawings is not able to show structures in a bend configuration. Correspondingly, the "bend" arms 933 are shown as hidden behind the surface which they actually engage. In a specific embodiment one of the additional actuation surfaces may be integrated into a clip, e.g. corresponding to clip 103 in FIG. 3. In a specific embodiment the non-free end of the clip may be connected to the housing by three supports along the length of the clip with gaps there between. The upper and lower supports primarily support the clip whereas the intermediate support is located over one of the actuation surface. This arrangement allows a user to squeeze the housing oval corresponding to the intermediate support of the clip.

The additional gripping means thus has an initial non-actuated state in which they provides a gripping engagement between the cap portion and a mounted needle cap which is sufficiently strong to hold the needle cap in gripping engagement with the cap portion after the needle cap has been removed from a hub mounted on the hub mount, or the hub on which the needle cap is mounted has been removed from the main portion, and sufficiently weak to allow the cap portion to be removed from the main portion without removing the needle cap from a hub mounted on the hub mount, and an actuated second state wherein there is no gripping engagement between the additional gripping means and the needle cap, this allowing the needle cap to be removed from the cap portion after the cap portion has been removed from the main portion, e.g. by means of gravity when the pen cap is hold upside-down.

Figure 7:
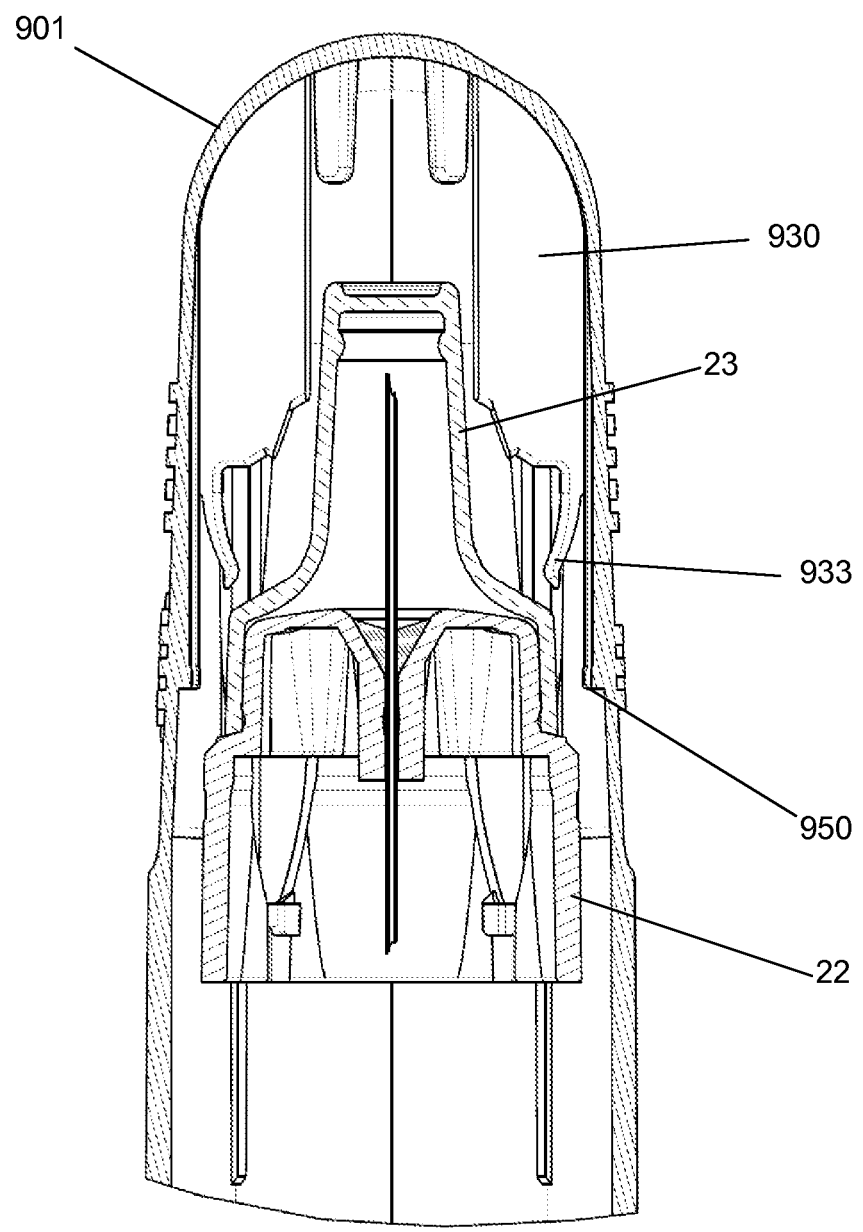
FIG. 7 shows the pen cap of FIG. 6 in which the needle assembly has been moved.
Figure 8:
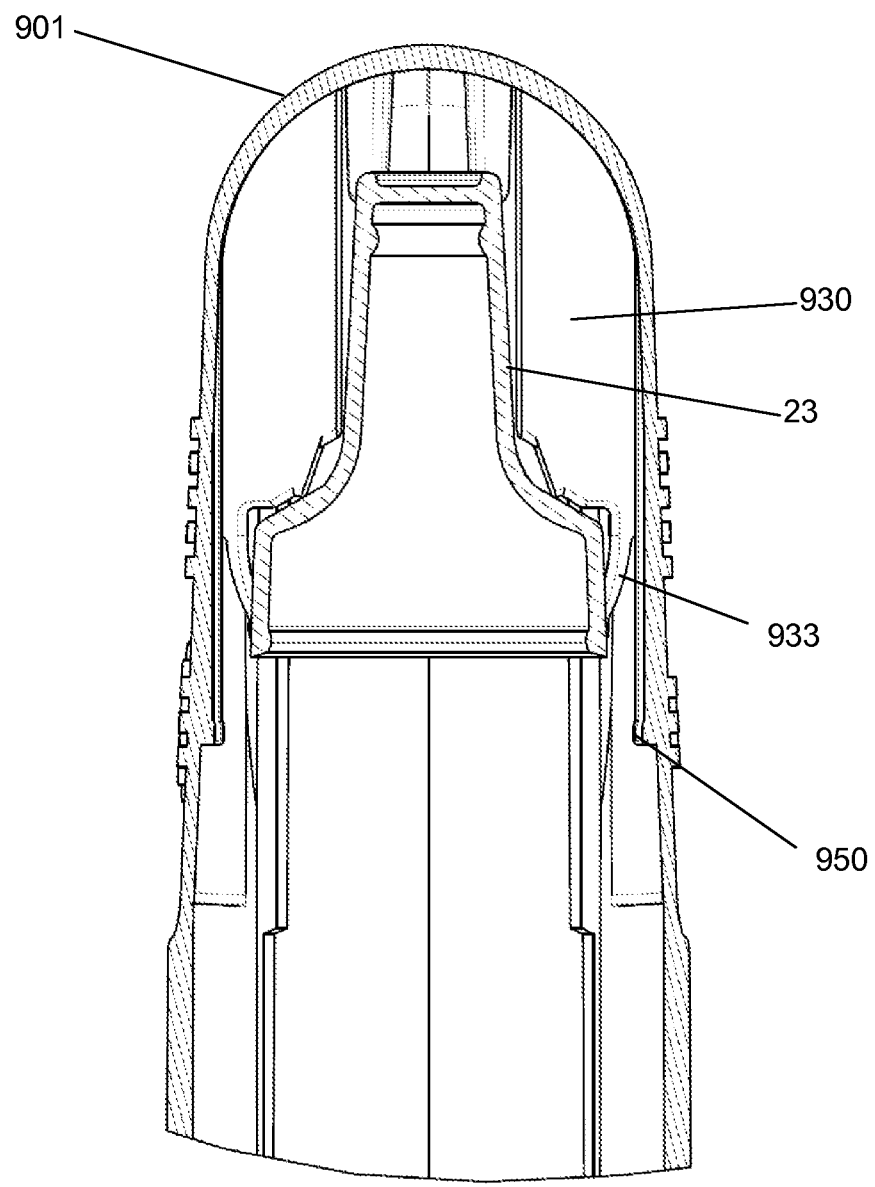
FIG. 8 shows the pen cap of FIG. 6 in which a needle cap is mounted.
Figure 9:
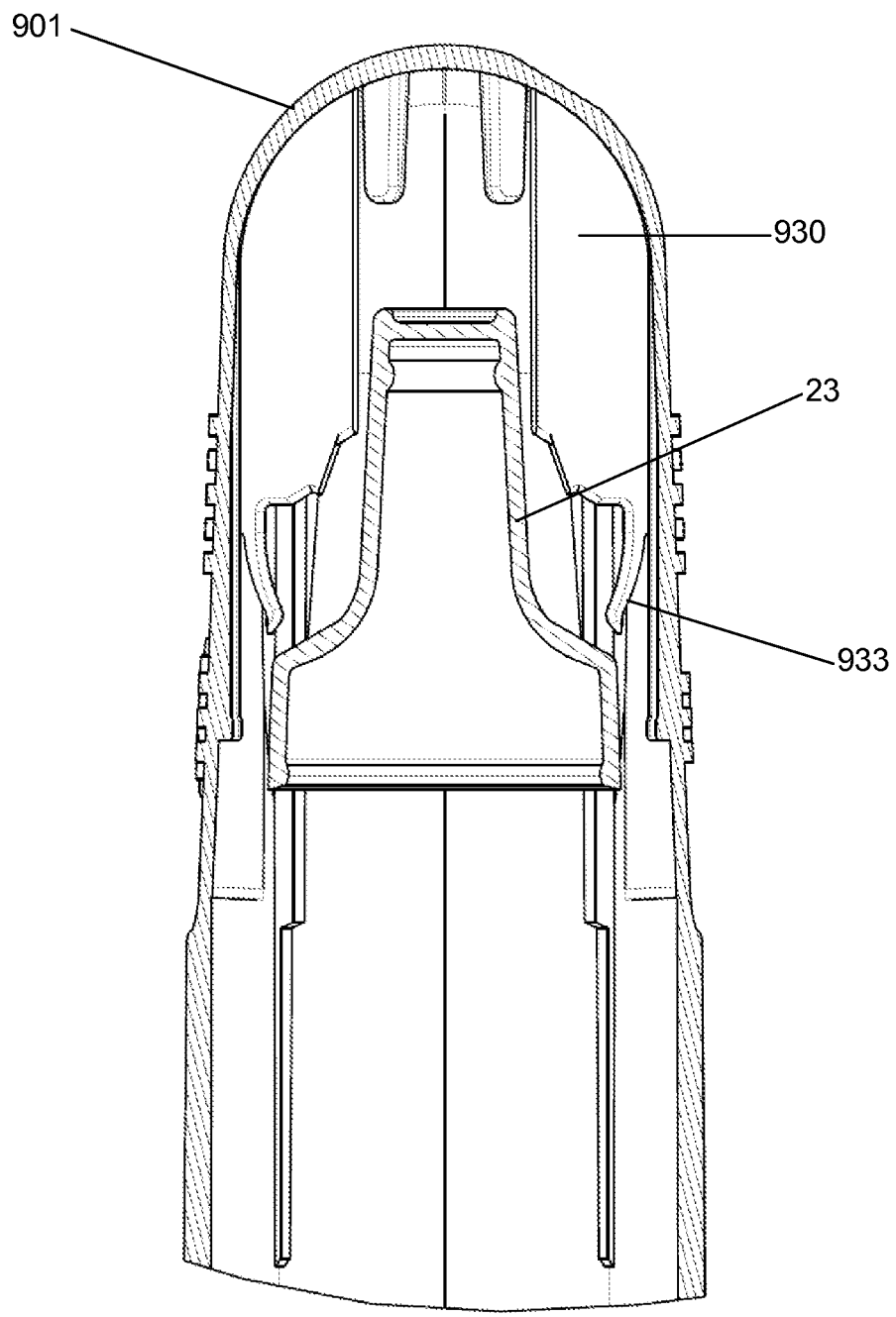
FIG. 9 shows the pen cap of FIG. 8 in which the needle cap has been moved.

Next, different situations of use will be described. FIG. 6 shows a needle assembly, comprising a needle hub 22 and a thereon mounted needle cap, positioned inside a pen cap corresponding to a situation of use in which both the needle assembly and the pen cap have been mounted on a main portion of a drug delivery system. The projections 932 ensure that the needle cap is correctly positioned axially. As appears, the first and second gripping means are in their non-actuated state, this allowing the pen cap to be removed from the main portion leaving both the needle hub and needle cap in place, the additionally gripping means thereby sliding out of engagement of with the needle cap as described above. FIG. 8 shows a situation in which the needle cap has been removed from the needle hub by actuation of the first gripping means, the needle cap being hold in place by the additional gripping means 933. As described above, this situation may have been reached by simultaneously actuating the first and second gripping means, the design of the second gripping means allowing the actuated second gripping means to be pulled out of engagement with the needle hub firmly connected to the main portion. When holding the pen cap upside-down and actuating the additional gripping means gravity will make the needle cap drop out as shown in FIG. 9 or, as shown in FIG. 7, together with a needle hub. In order to remove both a needle hub and a thereon mounted needle assembly the user first actuates the second gripping means (simultaneous actuation of the first gripping means will not influence this functionality) allowing the user to twist or turn the needle hub out of engagement with the hub mount of the main portion, and then axially pulls off the pen cap from the main portion. If the holding grip between the needle cap and the additional gripping means is designed correspondingly, it may not be necessary to actuate the second gripping means during the axial movement as the needle hub is moved axially via the needle cap. Indeed, if no needle cap is mounted then the second gripping means has to be actuated also during the axial movement of the pen cap just as the needle hub will not be hold in place inside the pen cap via the additional gripping means.

Summarizing the above disclosure, with reference to FIGS. 2-5 an embodiment of a pen cap having user actuated gripping means adapted to grip a needle cap was described, and with reference to FIGS. 6-10 an embodiment of a pen cap having user actuated gripping means adapted to grip both a needle cap and a needle hub was described. Turning to FIGS. 11-15 an embodiment of the present invention having user actuated gripping means adapted to grip a needle hub will be described.

Figure 11:
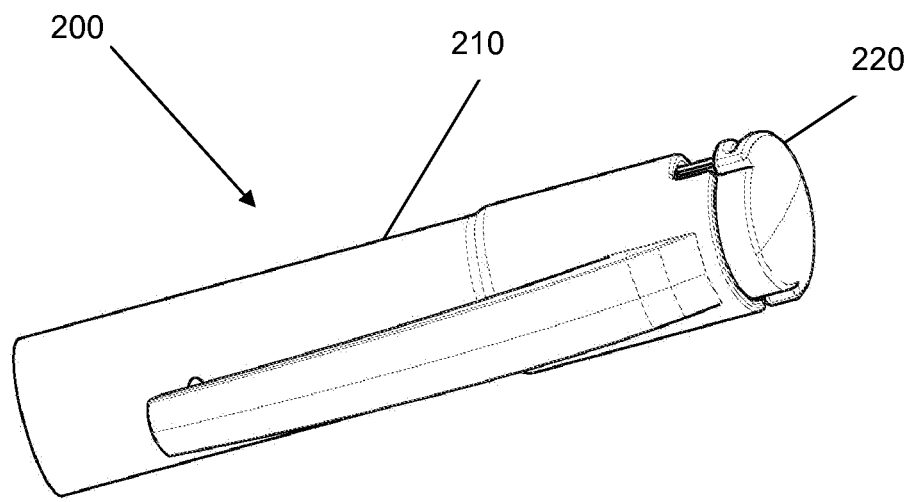
FIG. 11 shows a pen cap comprising a user-actuatable button.

FIG. 11 shows a pen cap 200 adapted to be used with a body portion of a pen-formed drug delivery device of the type shown in FIG. 1. The cap comprises a cap housing 210 provided with a user actuatable button 220 allowing the cap to engage with a mounted needle hub (see below).

Figure 12:
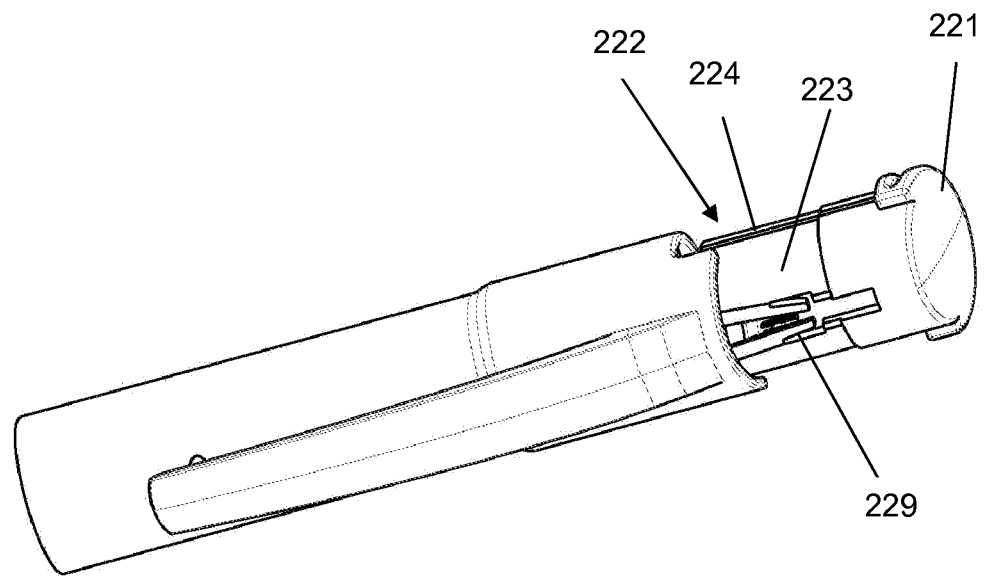
FIG. 12 shows the components of the pen cap shown in FIG. 11, FIGS. 13-15 show the pen cap of FIG. 11 in different stages of operation.

FIG. 12 shows the components of the pen cap before assembly. The button 220 comprises an upper top surface 221 allowing a user to exert an axial downwards force on the button as well as a skirt portion 221 divided into segments 223 by a number of axial slots 224. One of the slots is provided with a pair of opposed flexible arms 229 adapted to slide past an inner projection (spring support 215, see FIG. 13) on the cap housing yet preventing the two parts from being pulled apart after assembly.

Figure 13:
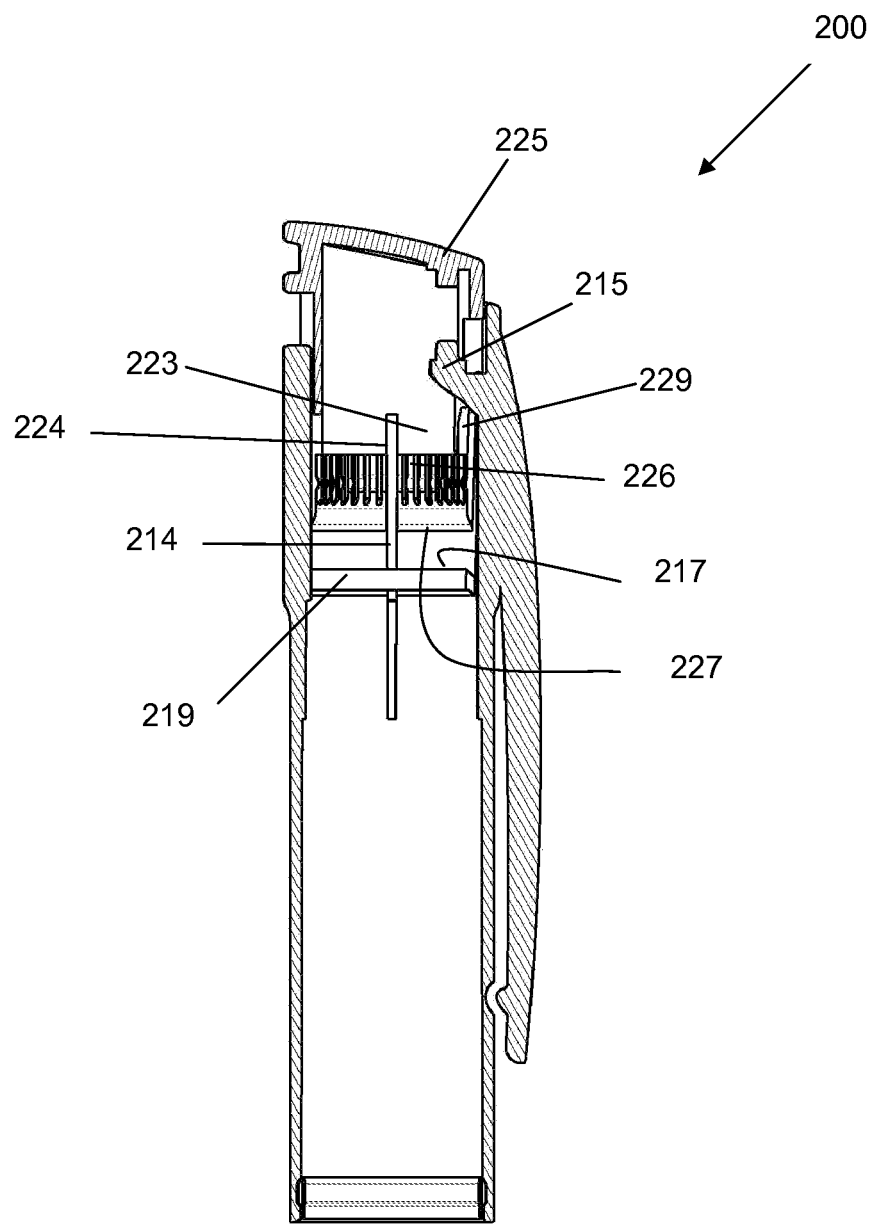
Figure 14:
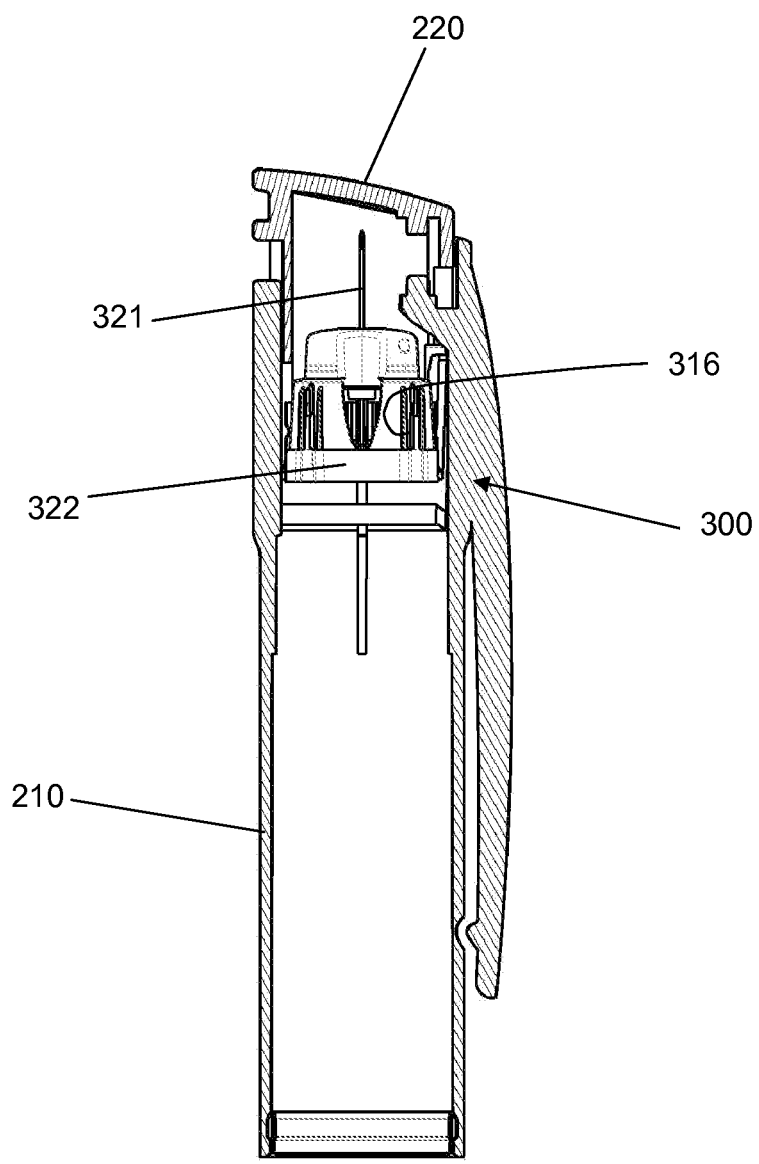

FIG. 13 shows a cross-sectional view of pen cap 200 comprising cap housing 210 provided with a user actuatable button 220 allowing the cap to engage with a mounted needle hub 300 (see FIG. 14). The button is guided axially in the housing by the slots 224 engaging axial housing ribs 214 allowing it to move between an initial fully extended "button up" position and a fully depressed "button down" position, a spring (not shown) supported between button spring support 225 and housing spring support 215 ensures that the button is biased towards its extended position. In the shown embodiment the skirt portion 222 is divided by four slots 224 into four 90 degrees segments 223. Each segment is provided with gripping means adapted to engage a portion of a mounted needle. In the shown embodiment each skirt segment is provided with a number of inwards facing ribs 226 adapted to axially engage outer ribs on the hub skirt 316 (see FIG. 14), this providing a rotational lock between the two components. The lower edges of the skirt segments are provided with an inclined downwards-inwards facing circumferential surface 227 adapted to axially engage a corresponding upwards-outwards facing inclined surface 217 on circumferential rib 219 arranged on the inner wall of the cap housing, this providing that the skirt segments are forced outwards when the button is forced downwards into engagement with the inclined surface(s) 216, this also providing a stop for the axial movement of the button.

Figure 15:
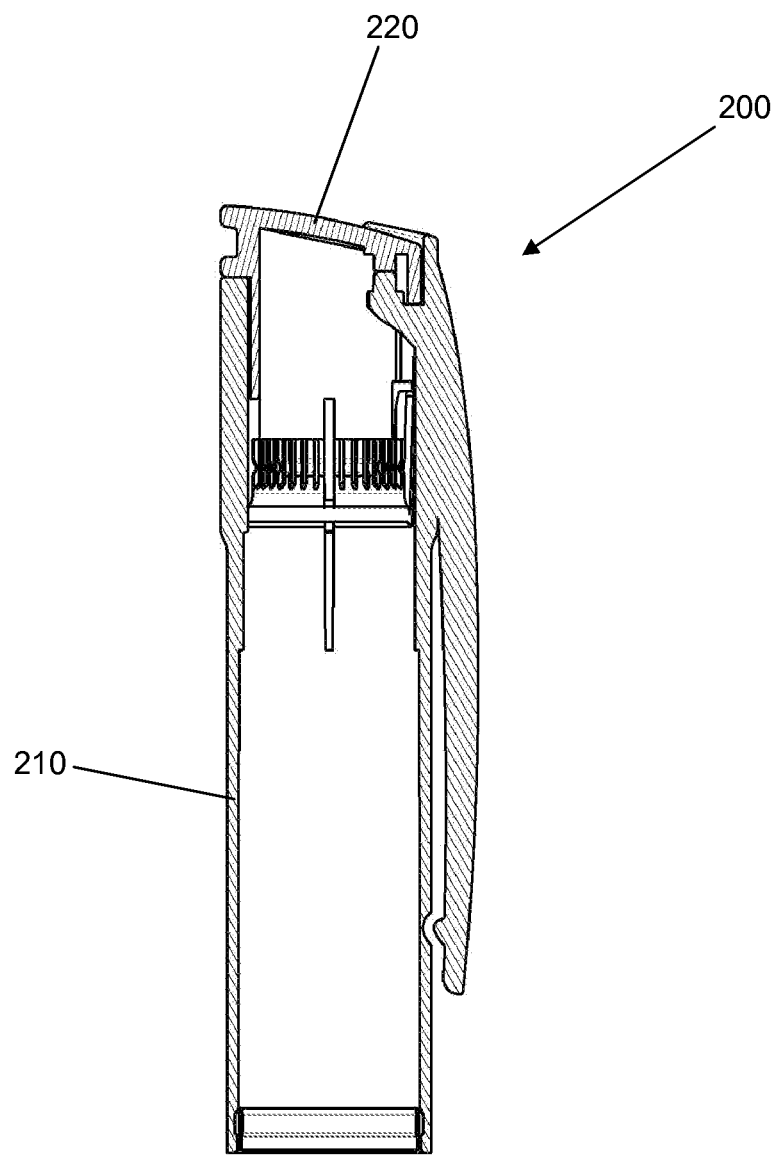

With reference to FIGS. 13-15 use of the pen cab 200 to assist in de-mounting a needle assembly from a pen body will be described.

FIG. 13 shows the cap button 210 in its initial upwards biased position. When the cap button is mounted on a pen body provided with a needle assembly 300 the needle hub 322 and needle 321 would be positioned relative to the cap housing as shown in FIG. 14. The pen cap is adapted to also accommodate a needle cap (not shown) when mounted therewith.

To de-mount the needle assembly the user first forces down the button until it meets a stop provided on the pen body (not shown) or when the user feels engagement between button and needle hub, the skirt segments thereby engaging and gripping the outer surface of the needle hub, see FIG. 14. Depending on the "strength" of the grip, e.g. by friction, and the return force provided by the spring the button may return to its initial position either when the user releases the force from the button or when the user actively pulls up the button. However, if the user rotates the pen cap relative to the pen body with the button depressed, the needle hub will be rotated relative to the pen body, this allowing the needle hub to be unscrewed from the pen body. In case the coupling between the needle assembly and the pen body is a traditional thread several rotations of the cap will be necessary, however, if the coupling is of the bayonet type only a short twist will be necessary. In case a traditional thread is used the needle hub will be allowed to move axially between the skirt segments as the hub is rotated off the pen body with the needle being moved fully or partly out of the drug cartridge. When the needle assembly has been un-coupled from the pen body the user can remove the pen cap from the pen body together with the needle assembly which is hold in gripping engagement by the skirt segments. To remove the needle assembly from the pen cap the user now fully depresses the pen button whereby the lower edges of the skirt segments engage the inclined surface(s) on the cap housing (see FIG. 15), this forcing the skirt segments outwards and thus out of engagement with the needle hub (not shown in FIG. 15), thereby allowing the needle assembly to be removed from the needle cap, e.g. by means of gravity. When the needle assembly is released from the cap and the user releases the pressure from the button, the button will be returned to its initial position by spring 230.

In other words, the shown pen cap is operated between (i) a first state in which there is no gripping engagement between the mounted pen cap and a needle hub when a needle assembly is mounted on the pen body, (ii) a second state in which the mounted pen cap grippingly engages a needle hub of a needle assembly mounted on the pen body, this allowing a needle assembly to be de-mounted and removed from the pen body together with the pen cap when the pen cap is removed from the pen body, and (iii) a third state in which a needle hub held in gripping engagement with the pen cap via the gripping means is released from the gripping means, this allowing the needle assembly to be removed from the pen cap.

With reference to FIGS. 11-15 a first embodiment of a pen cap incorporating the principle of the present invention is shown, however, the principle can be realized by many other arrangements providing the desired functionality of engaging and disengaging a needle hub in order to remove it from a main portion of a drug delivery device, e.g. a pen body. A number of such alternatives are shown in FIGS. 16-20.

More specifically, FIG. 16 shows an embodiment of a drug delivery device 400 comprising a pen body 403 and a pen cap 410 having a single user operated push button 420 as in the above-described embodiment, however, a mechanism is provided in which a first push on the button will lock the needle hub rotationally and axially to the pen cap making it possible to unscrew the needle. After unscrewing the needle hub it will stay in the device cap. A second push on the button will release the needle hub from the cap and a third push on the button will return the button to its initial position. As appears, this embodiment provides a user interface resembling a typical ball pen mechanism.

FIG. 17 shows an embodiment of drug delivery device 500 with a pen cap 510 comprising first and second user operated push buttons 521, 522. A first push on the first button 521 will lock the needle hub rotationally and axially to the pen cap making it possible to unscrew the needle. After unscrewing the needle hub it will stay in the device cap. A second push on the second button 522 will release the needle hub from the cap after which the cap is returned to its initial position.

FIG. 18 shows an embodiment of drug delivery device 600 with a pen cap 610 comprising first and second user operated push buttons 621, 622. A first push on the first button 621 will lock the needle hub rotationally and axially to the pen cap making it possible to unscrew the needle. After unscrewing the needle hub it will stay in the device cap. A second push on the second button 622 will release the needle hub from the cap after which the cap is returned to its initial position.

FIG. 19 shows an embodiment of drug delivery device 700 with a pen cap 710 comprising a user operated ring member 721 and a user operated push button 722. Pushing the button down will lock the needle hub rotationally and axially to the pen cap making it possible to unscrew the needle. After unscrewing the needle, it will stay in the device cap. Twisting the ring member, e.g. clockwise, will release the needle hub from the cap after which the cap is returned to its initial position, e.g. by the user rotating the ring member back to its initial position or by a spring rotating the ring member back to its initial position.

FIG. 20 shows an embodiment of drug delivery device 800 with a pen cap 810 comprising a single user operated ring member 820. Rotating the ring member in a first direction, e.g. counter clockwise, will lock the needle hub rotationally and axially to the pen cap making it possible to unscrew the needle. After unscrewing the needle, it will stay in the device cap. Rotating the ring member in the opposite direction, i.e. clockwise, will release the needle hub from the cap after which the cap is returned to its initial position, e.g. by the user rotating the ring member back to its initial position or by a spring rotating the ring member back to its initial position.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery system comprising:
(a) a main portion comprising:
a drug reservoir or means for receiving a drug reservoir, and
drug expelling means for expelling drug from the reservoir,
(b) a needle assembly comprising:
a needle hub adapted to be mounted on the main portion,
a hollow needle mounted in the needle hub and comprising a distal pointed end and a proximal end, the proximal end being adapted to be arranged in fluid communication with the reservoir when the hub is mounted on the main portion, and
a needle cap releasably mountable on the hub to cover the distal pointed end,
(c) a cap portion releasably mountable to the main portion and comprising:
first gripping means reversibly operatable between:
(i) a first state in which there is no gripping engagement between the first gripping means of a mounted cap portion and a given first part of a needle assembly when the needle assembly is mounted on the main portion, this allowing the cap portion to be removed from the main portion without removing the given first part from the main portion, and
(ii) a second state in which the first gripping means of the cap portion grippingly can engage the given first part of a needle assembly mounted on the main portion, this allowing the cap portion to be removed from the main portion together with the given first part when the cap portion is removed from the main portion, and first user actuation means for operating the first gripping means between the two states.

2. A drug delivery system as in claim 1, wherein the given first part is a needle cap.

3. A drug delivery system as in claim 2, wherein the cap portion comprises:
second gripping means reversibly operatable between:
(i) a first state in which there is no gripping engagement between the second gripping means of a mounted cap portion and a needle hub of a needle assembly when the needle assembly is mounted on the main portion, this allowing the cap portion to be removed from the main portion without removing the needle hub from the main portion, and
(ii) a second state in which the second gripping means of the cap portion grippingly can engage the needle hub of a needle assembly mounted on the main portion, this allowing the needle hub to be demounted from the main portion and the cap portion to be removed from the main portion together with the demounted needle hub, and
second user actuation means for operating the second gripping means between the two states.

4. A drug delivery system as in claim 3, wherein the first and second user actuation means are combined in a common user actuation means serving to actuate both the first and second gripping means.

5. A drug delivery system as in claim 4, wherein the second gripping means in their actuated state is be adapted to disengage a mounted needle hub when the cap portion is removed from the main portion.

6. A drug delivery system as in claim 2, the cap portion comprising additional gripping means adapted to provide a gripping engagement between the cap portion and a mounted needle cap, the additional gripping means providing a grip which is:
(a) sufficiently strong to hold a needle cap in gripping engagement with the cap portion after a needle cap has been removed from a needle hub mounted on the main portion, and
(b) sufficiently weak to allow the cap portion to be removed from the main portion without removing a needle cap from a needle hub mounted on the main portion.

7. A drug delivery system as in claim 2, the cap portion comprising:
additional gripping means reversibly operatable between:
(i) a first state in which the additional gripping means provides a gripping engagement between the cap portion and a mounted needle cap which is:
(a) sufficiently strong to hold the needle cap in gripping engagement with the cap portion after the needle cap has been removed from a needle hub mounted on the main portion, or the needle hub on which the needle cap is mounted has been removed from the main portion, and
(b) sufficiently weak to allow the cap portion to be removed from the main portion without removing the needle cap from a needle hub mounted on the main portion, and
(ii) a second state in which there is no gripping engagement between the additional gripping means and the needle cap, this allowing the needle cap to be removed from the cap portion after the cap portion has been removed from the main portion, and
additional user actuation means for operating the additional gripping means between the two states.

8. A drug delivery system as in claim 1, wherein the cap portion has an initial state in which at least one gripping means is in the first state, and an actuated state in which the at least one gripping means is in the second state.

9. A drug delivery system as in claim 1, wherein the cap portion comprises an outer housing portion with at least one pair of actuation areas serving as actuation means for associated gripping means, wherein movement of a pair of actuation areas towards each other operates the associated gripping means between the initial and the actuated state.

10. A drug delivery system as in claim 9, wherein the outer housing portion is flexible and at least one gripping means is formed integrally therewith, whereby actuation of the at least one gripping means is based on flexible deformation of the outer housing portion by means of the associated pair of actuation areas.

11. A drug delivery system as in claim 1, wherein the given first part is a needle hub and the first gripping means is reversibly operatable between:
  (i) a first state in which there is no gripping engagement between the mounted cap portion and a needle hub when a needle assembly is mounted on the main portion,
  (ii) a second state in which the mounted cap portion grippingly engages a needle hub of a needle assembly mounted on the main portion, this allowing the needle assembly to be de-mounted and removed from the main portion together with the cap portion when the cap portion is removed from the main portion, and
  (iii) a third state in which a needle hub held in gripping engagement by the gripping means is released from the gripping means, this allowing the needle assembly to be removed from the cap portion, and
  the first user actuation means is adapted for operating the first gripping means between the three states.

12. A drug delivery system as in claim 11, wherein the first gripping means can be locked in the second state.

13. A drug delivery system as in claim 12, wherein the cap portion comprises a cap body having release means, the first gripping means being operated between its second and third states by movement of the gripping means relative to the cap body release means.

14. A drug delivery system as in claim 1, wherein the cap portion comprises one or more inspection openings or windows allowing a user to inspect at least a portion of a mounted needle assembly.

* * * * *